United States Patent [19]

Shirato et al.

[11] Patent Number: 4,680,552
[45] Date of Patent: Jul. 14, 1987

[54] APPARATUS FOR MEASURING IMPURITIES IN SUPER-PURE WATER WITHOUT EXPOSURE TO SURROUNDING ATMOSPHERE

[75] Inventors: Kozo Shirato, Omiya; Kazuo Hiraizumi, Narashino; Kazuyasu Kawashima, Yokohama; Shinya Okuyama; Masashi Kobayashi, both of Tokyo; Minoru Tanaka, Kawaguchi; Akira Takeya, Tokyo; Yoshio Yamamoto, Kawaguchi; Yasuo Koyama, Warabi; Satoshi Shinohara; Toru Yunoki, both of Chigasaki, all of Japan

[73] Assignees: Erma Optical Works, Ltd., Tokyo; Ulvac Service Corporation, Kanagawa, both of Japan

[21] Appl. No.: 702,641

[22] Filed: Feb. 19, 1985

[30] Foreign Application Priority Data

Nov. 21, 1984 [JP] Japan .................. 59-247535

[51] Int. Cl.$^4$ ............ G01N 27/02; G01N 27/00; G01N 27/28
[52] U.S. Cl. .................. 324/439; 324/71.4; 324/450
[58] Field of Search ............ 324/439, 444, 450, 71.4; 210/900; 203/3, 1

[56] References Cited

U.S. PATENT DOCUMENTS 2,656,508  10/1953  Coulter ........................ 324/439
3,921,006  11/1975  Pontigny ...................... 307/118
4,025,307   5/1977  Randolph et al. .............. 324/71.4
4,580,093   4/1986  Feier et al. .................. 324/71.4

Primary Examiner—Reinhard J. Eisenzopf
Assistant Examiner—Vinh P. Nguyen
Attorney, Agent, or Firm—Watson, Cole, Grindle & Watson

[57] ABSTRACT

A measuring apparatus for measuring the number and size of impurities such as dust and bacteria in super-pure water includes a sealed container; a sample supply line which sealingly interconnects a source of super-pure water with the sealed container and supplies a sample mixture of super-pure water and electrolyte to the sealed container; an overflow pipe which sealingly connects with the side of the sealed container; a negative electrode which extends into the sample mixture in the sealed container; a hollow sensor which extends into the sample mixture in the sealed container, the hollow sensor containing a positive electrode surrounded by electrolyte and having a small hole at its lower end; and a detecting circuit connected to said negative and positive electrodes for supplying a certain DC current therebetween and detecting voltage pulses caused by impurities passing through the small hole into the hollow sensor.

4 Claims, 1 Drawing Figure

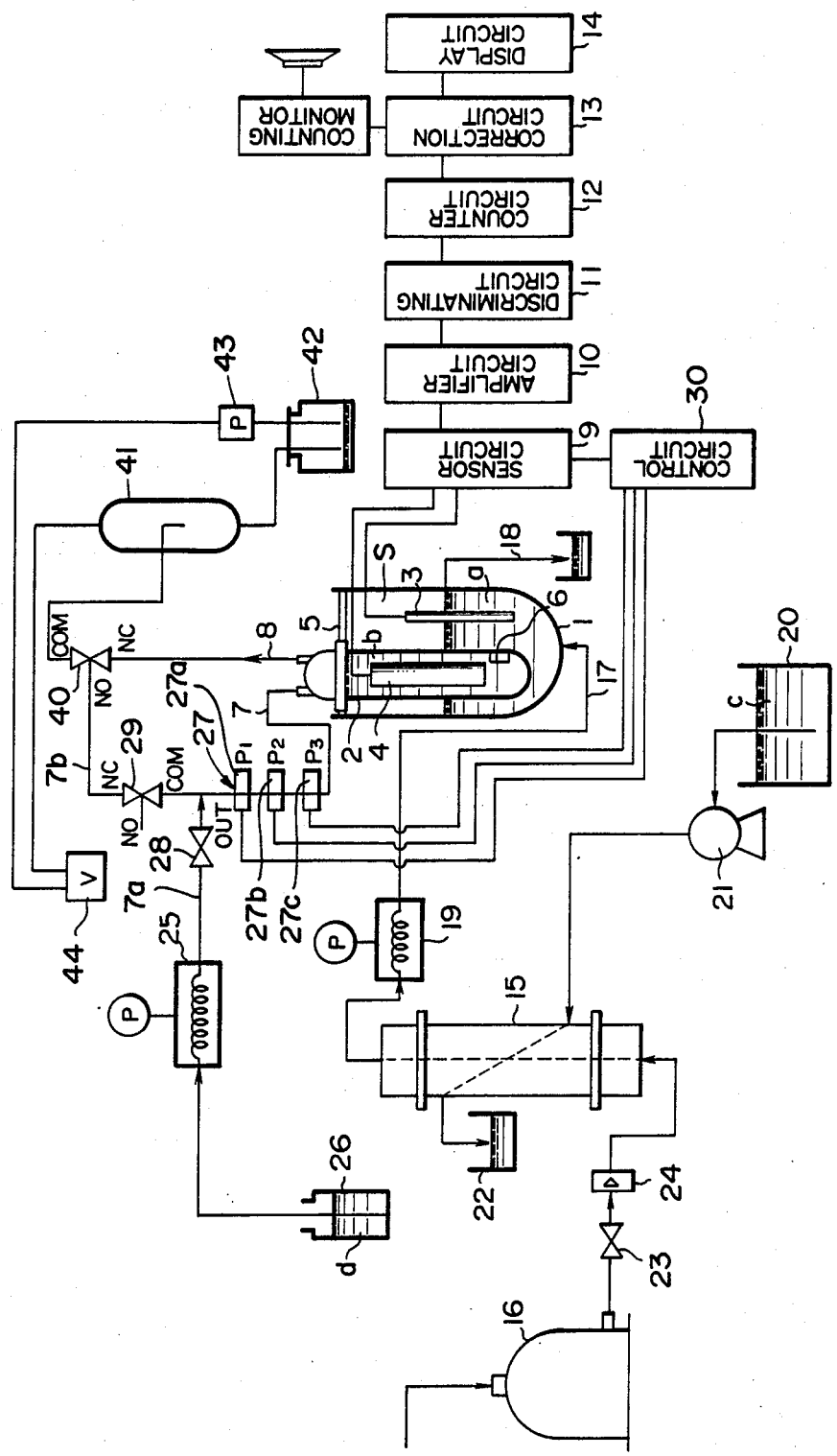

APPARATUS FOR MEASURING IMPURITIES IN SUPER-PURE WATER WITHOUT EXPOSURE TO SURROUNDING ATMOSPHERE

BACKGROUND OF THE INVENTION

1. Field of the Invention

The present invention relates to a measuring apparatus which can measure the number and sizes of impurities such as fine dust and bacteria in super-pure water, and more particularly to such a measuring apparatus which determines the number and sizes of the impurities by determining the variation in the electrical resistance between a positive and a negative electrode, the negative electrode being immersed in a sample mixture of the super-pure water and an electrolyte, and the positive electrode being mounted within a hollow sensor which is immersed in the sample mixture, the hollow sensor also containing an electrolyte and having a small hole at its lower end.

2. The Prior Art

A measuring apparatus of the above-noted type which is capable of making measurements of the number and sizes of impurities in separate batches of super-pure water is known. This apparatus includes an open-topped sample container in which the sample batches of super-pure water (containing an electrolyte) are poured; a negative electrode extending into the sample batches; a hollow sensor extending into the sample batches, the hollow sensor having a small hole at its lower end and containing a positive electrode surrounded by electrolyte; means for suitably supplying and removing electrolyte from the hollow sensor; and electrical means connected to the positive and negative electrodes to cause a certain DC to flow therebetween and to detect variations in the resistance (voltage pulses) therebetween which result from impurities passing from the sample batch in the container through the small hole in the hollow sensor. However, because the samples are measured batchwise, they are always exposed to the surrounding atmosphere prior to being measured by the measuring apparatus. As such, these batches will pick up dust and/or bacteria from the surrounding atmosphere, and the subsequent (or contemporaneous) measurement of number and sizes of impurities in the super-pure water will not be representative of the number and sizes of impurities of the super-pure water in its initial condition. This will be less of a problem if the measurements are conducted in a room containing purified air (a "clean room"). However, such clean rooms are very expensive to provide and maintain. In addition, even in a clean room the samples will be exposed to the air therein, and they will thus necessarily contained dissolved nitrogen, which will produce incorrect impurity measurements.

SUMMARY OF THE INVENTION

It is an object of the present invention to provide a measuring apparatus for measuring the number and sizes of impurities in super-pure water which will be more accurate than the known measuring apparatus and which can be used in a normal room.

According to the present invention the measuring apparatus includes a sealed container for the super-pure water mixed with electrolyte and a sample supply line which sealingly extends between the source of the super-pure water and the sealed container. As such, the super-pure water is not exposed to the surrounding atmosphere prior to its being fed to the sealed container or while contained therein. The sample supply line advantageously includes a dialysis device where the super-pure water is mixed with electrolyte and a deaerating device where the dissolved gases in the sample mixture of super-pure water and electrolyte are removed. The sample supply line is capable of supplying a continuous flow of sample mixture to the sealed container.

The invention will now be better understood by reference to the attached figure, taken in conjunction with the following dicussion.

DESCRIPTION OF THE FIGURE

The attached FIGURE schematically shows a preferred embodiment of a measuring apparatus according to the present invention.

DETAILED DESCRIPTION OF THE PREFERRED EMBODIMENT

The measuring apparatus shown in the FIGURE, which can be used to measure the amount of particulate impurities in super-pure water contained in a source tank 16 without the super-pure water being exposed to the surrounding atmosphere at any time prior to measurement, includes an upwardly open measuring container 1 which has an inlet opening 1a at its bottom and an outlet opening 1b along its side, and a lid 5 which sealingly covers the upper end of the container 1 from the surrounding atmosphere so as to provide an interior space S therein which is isolated from the surrounding atmosphere. The measuring container 1 is composed of an electrically insulating material, e.g., glass. A sample supply line 17 is sealingly connected to the inlet opening 1a of the container 1 so as to supply a sample mixture a of super-pure water and electrolyte to the container 1, and an overflow pipe 18 is sealingly connected to the outlet opening 1b to remove the mixture from the container to a sample drain tank. The surface level of the sample mixture a in the container 1 will always be level with the outlet opening 1b.

A hollow sensor 2 which is composed of an electrically-insulating material, i.e., glass, sealingly extends downwardly through the lid 5 and into the container 1 such that its lower end is immersed in the sample mixture a. The wall of the sensor 2 includes a small hole 6 at its lower end (the hole diameter is about 10 $\mu$m) in which a rubby or sapphire chip is fitted so as to control the flow of impurity particles therethrough. A cap 2a covers the upper end of the sensor 2, the cap including two openings therein. An electrolyte supply line 7 is sealingly connected to one of these openings and an electrolyte discharge line 8 is sealingly connected to the other.

Mounted within the sensor 2 is an inner (positive) electrode 4, this electrode being surrounded by electrolyte b. A separate outer (negative) electrode 3 is mounted within the container 2 such that its bottom is immersed in the mixture a. Each of the electrodes 3 and 4 are electrically connected to a sensor (pulse-detecting) circuit 9. A certain DC current is caused to flow between the electrodes 3 and 4. The sensor circuit 9 is electrically connected in series with an amplifier circuit 10, a discriminating circuit 11, a counter circuit 12 and a correction circuit 13, and the correction circuit 13 is separately electrically connected to a counting monitor and a display circuit 14. A control circuit 30 is connected to the sensor circuit 10. Its function will be referred to below.

The sample supply line 17 is connected at its upstream end to the source tank 16 containing super-pure water, and connected along the sample supply line are a flow valve 23, a flow meter 24, a dialysis device 15 and a deaerating device 19. The super-pure water from the source tank 16 flows through the flow valve 23 and the flow meter 24 and into the dialysis device 15 where it is mixed with an electrolyte, e.g., brine. In this regard, the dialysis device 15 contains a bundle of semipermeable hollow fibers, e.g., tubular polyvinylalcohol fibers, through which the super-pure water passes, the super-pure water concurrently being mixed with the brine which passes through the walls of the hollow fibers. The brine c is supplied to the dialysis device 15 from a brine tank 20 via a pump 21, and the excess brine is discharged into a drain tank 22. The brine c in the brine tank 20 can have a salt concentration of 20%. The sample mixture of super-pure water and brine (e.g., super-pure water containing up to 15% brine) leaving the dialysis device 15 passes through a deaerating device 19 where the dissolved gases therein are removed, and then into the container 1. The deaerating device 19, which is itself well known, includes tubes which are permeable only to gases. The vacuum created by the pump P of the deaerating device causes dissolved gases to pass out of the sample mixture as it moves through the tubes.

The upstream end of the electrolyte supply line 7 includes two branch lines 7a and 7b. Branch line 7a is connected to an electrolyte supply bottle 26 containing electrolyte d, and connected along this branch 7a are a deaerating device 25 and a flow valve 28. Branch line 7b is connected to a three-way electromagnetic valve 40 in the electrolyte discharge line 8 via a three-way electromagnetic valve 29. The supply line 17 includes a manometer 27 downstream of the branches 7a and 7b. The manometer includes photosensors 27a, 27b and 27c at levels $P_1$, $P_2$ and $P_3$ for measuring the electrolyte level therein. The photosensors 27a, 27b and 27c are each electrically connected to the control circuit 30.

The electrolyte discharge line 8 extends into a glass tank 41 via a three-way electromagnetic valve 40. The glass tank 41 communicates with an exhaust bottle 42 and a vacuum pump 43 is connected to the exhaust bottle 42. A pressure sensor 44 is connected to the glass tank 41 and the vacuum pump 43 to maintain the interior of the exhaust bottle 42 at a given negative pressure.

The inventive measuring apparatus operates as follows. Electrolyte d in the electrolyte supple bottle 26 is supplied to the sensor 2 via the electrolyte supply line 7. In this regard, a switch (not shown) is positioned in an "on" mode, such that the valve 28 is opened and the NC and COM sides of the three-way electromagnetic valve 40 are opened. Due to the suction created by vacuum pump 43, the electrolyte d in the electrolyte supply bottle 26 will flow through the deaerating device 25 (where dissolved gases therein are removed) and then through the valve 28, the manometer 27 and into the sensor 2. In the meantime, deaerated electrolyte in the sensor 2 is caused to flow through the drain pipe 8 and the valve 40 to the glass tank 41 and finally into the exhaust bottle 42. The electrolyte supply line 7 and exhaust line 8 become filled with deaerated electrolyte d.

Subsequently, the valve 28 is closed. Valve 23 is then opened, and super-pure water from the source tank 16 flows into the sample supply line 17 and passes through the flow valve 23, the flow meter 24 and the dialysis device 15 where a certain amount of electrolyte is mixed therewith. Thereafter, the sample mixture flows through the deaerating device 19 where dissolved gases are removed and then into the bottom of the container 1 to provide the sample mixture a therein. The excess sample mixture in the container 1 is discharged via the overflow pipe 18.

When a measurement switch (not shown) is positioned in an "on" mode, the valve 28 is closed, and the NC and the COM sides of the valve 40 are opened. At the same time, the NC and COM sides of the valve 29 are opened. Then, the electrolyte in the electrolyte liquid circuit is drawn from the drain pipe 8 connected to the sensor 2 to the exhaust bottle 42 through the glass tank 17 due to the suction force of the vacuum pump 43. At the same time, air is introduced into the electrolyte liquid circuit from the NO side of the valve 29, and the electrolyte liquid level in the manometer 27 is lowered to level $P_3$ through level $P_1$. When the liquid level in the manometer 27 reaches level $P_3$, a photosensor 27c is turned on. At this time, valve 40 is closed and the NO and COM sides thereof opened. Also, the NO side of the valve 29 is closed and the COM and NC sides thereof opened. The liquid level in the manometer rises due to the suction of pump 43. Since the interior of the sensor 2 is kept at a negative pressure, some of the sample mixture a in the container 1 will be drawn through the small hole 6 into the sensor 2. When the liquid level in the manometer reaches level $P_2$, a photosensor 27b is turned on. The sensor circuit 9, amplifier circuit 10, discriminating circuit 11, counter circuit 12, correction circuit 13, counting monitor and display circuit 14 are all turned on via the control circuit 30. When the sample mixture a containing super-pure water is drawn into the sensor 2, so are the impurities therein. When an impurity passes through the small hole 6 of the sensor 2, the resistance between the electrodes 3 and 4 is instantaneously increased, and an electrical pulse having an amplitude proportional to the size of the impurity is generated. The pulse is detected by the sensor circuit 9 and is processed by the amplifier circuit 10 the discriminating circuit 11, the counter circuit 12 and the correction circuit 13. The number of impurities is digitally displayed on the counter circuit 14.

When the liquid level in the manometer 27 reaches level $P_1$, the photosensor 27a is turned on and the measurement is terminated. While the liquid level in the manometer 27 rises from level $P_2$ to level $P_1$, the amount of the super-pure water drawn into the sensor 2 through the small hole 6 reaches the unit suction amount. Thus, the number of impurities contained in the unit suction amount of super-pure water is counted. It should be noted that the sample mixture can be continuously supplied to the container 1 via the supply line 17 and continuously removed therefrom via the overflow pipe 18 while the foregoing measurement is made.

Because the container 1 is insulated from the surrounding atmosphere by lid 5 and because the sample supply line 17 is sealingly connected between the source tank 16 and the container 1 such that the super-pure water flowing therethrough is never exposed to the surrounding atmosphere, no dust or bacteria from the surrounding atomsphere can mix with the super-pure water and thus provide an erroneous measurement of the impurities therein. Nor can gases such as nitrogen become dissolved therein. In addition, because the sample supply line 17 includes a deaerating device for deaerating the mixture of super-pure water and electrolyte prior to being fed to the container 1, it is possible to eliminate most if not all dissolved gases in the mixture. As such, the measurement made in container 1 will provide a very accurate measurement of the number and sizes of impurities pure unit suction amount of the super-pure water obtained from the source tank 16.

It should also be noted that the continuous feed of sample mixture to and from the container 1 helps reduce any incorrect impurity measurement values being obtained to multiplication of the bacteria in the sample mixture which might occur with the sample mixture residing in the container 1 for any significant period of time.

While one preferred embodiment of the inventive apparatus has been shown and described, it is obvious that modifications can be made therein and still fall within the scope of the appended claims.

What is claimed is:

1. An apparatus for measuring the impurities in super-pure water taken from a source of super-pure water without the super-pure water being exposed to the surrounding atmosphere prior to the measurement, said apparatus including
    a sealed container which defines an interior space which is isolated from said surrounding atmosphere,
    a sample supply means sealingly connected between said source of super-pure water and said sealed container so as to feed a sample mixture containing super-pure water into the interior space in said container,
    an overflow pipe sealingly connected to said sealed container to remove excess sample mixture from the interior space in said container,
    a sensor circuit,
    a negtaive electrode located in the interior space in said sealed container and extending into the sample mixture in the interior space in said sealed container, said negative electrode being electrically connected to said sensor circuit,
    a hollow sensor tube sealingly extending into the interior space in said container such that a lower end thereof is in said sample mixture, said lower end including a small hole therein,
    a positive electrode located in said hollow sensor tube, said positive electrode being electrically connected to said sensor circuit,
    means for applying a constant DC voltage through said negative and positive electrodes,
    means for supplying an electrolyte to said hollow sensor tube to surround said positive electrode therein, and
    means for removing the electrolyte from said hollow sensor tube.

2. The apparatus as defined in claim 1, wherein said sample supply means includes a dialysis device through which the super-pure water flows and wherein said super-pure water is mixed with an electrolyte to form said sample mixture.

3. The apparatus as defined in claim 2, wherein said sample supply means also includes a deaerator device therein between said dialysis device and said sealed container for removing dissolved gases in said sample mixture of super-pure water mixed with electrolyte.

4. The apparatus as defined in claim 1, wherein said sensor circuit is electrically connected in series with an amplifier circuit, a discriminating circuit, a counter circuit and a correction circuit, and wherein said correction circuit is electrically connected to a counting monitor and a display unit.

* * * * *